United States Patent [19]

Montaldi

[11] Patent Number: 4,700,701

[45] Date of Patent: Oct. 20, 1987

[54] STERILIZATION METHOD AND APPARATUS

[76] Inventor: David H. Montaldi, 800 W. Jefferson, Kirksville, Mo. 63501

[21] Appl. No.: 790,532

[22] Filed: Oct. 23, 1985

[51] Int. Cl.[4] .............................................. A61B 17/36
[52] U.S. Cl. .................................. 128/303.17; 604/55
[58] Field of Search ............ 128/1 R, 127, 130, 303.1, 128/303.17, 399–402; 604/55, 60

[56] References Cited

U.S. PATENT DOCUMENTS

| | | | |
|---|---|---|---|
| 3,042,030 | 7/1962 | Read | 128/1.3 |
| 3,142,158 | 7/1964 | Podolsky | 128/399 |
| 3,163,165 | 12/1964 | Isirawa | 128/303.17 |
| 3,502,080 | 3/1970 | Hirschhorn | 128/303.1 |
| 3,572,335 | 3/1971 | Robinson | 604/55 |
| 3,805,767 | 4/1974 | Erb | 128/1 R |
| 3,810,458 | 5/1974 | Semp | 128/1 R |
| 3,918,431 | 11/1975 | Sinnreich | 128/1 R |
| 3,946,734 | 3/1976 | Dedrick et al. | 128/1 R |
| 4,057,063 | 11/1977 | Gieles et al. | 128/303.17 |
| 4,136,695 | 1/1979 | Dafoe | 128/1 R |
| 4,185,618 | 1/1980 | Corey | 604/55 |
| 4,245,623 | 1/1981 | Erb | 128/1 R |
| 4,483,341 | 11/1984 | Witteles | 128/303.1 |
| 4,523,590 | 6/1985 | Roth et al. | 128/1 R |
| 4,537,186 | 8/1985 | Verschof et al. | 128/130 |

FOREIGN PATENT DOCUMENTS 2452695  5/1976  Fed. Rep. of Germany ....................... 128/303.17

Primary Examiner—Kyle L. Howell
Assistant Examiner—Max F. Hindenburg
Attorney, Agent, or Firm—Leitner, Greene & Christensen

[57] ABSTRACT

There has been provided a method and apparatus for sterilizing females. Cautery means, vaginally insertable into the fallopian tube of the female, destroys a portion of said mucosal lining at a selected location. An absorbable scarification means and plug means is placed in the fallopian tube at said selected location. As the scarification means is absorbed, the fallopian tube forms scar tissue radially from a muscular layer thereof whereby the fallopian tube is blocked. The plug means blocks peritoneal infiltration of the by-products of cauterization and scarification outside the fallopian tube during the absorption interval.

26 Claims, 4 Drawing Figures

STERILIZATION METHOD AND APPARATUS

BACKGROUND OF THE INVENTION

A variety of birth control methods have been utilized in the past in an attempt to prevent undesired conception. Some methods are purely mechanical or involve the implantation of devices which interfere with conception. The present invention is not directed to these methods. Also, the drastic remedy of surgically removing reproductive organs is not the object of the present invention. As hereinafter described, the present invention is directed to a surgical technique which is simple to perform, safe, effective, reversible and relatively inexpensive.

The invention is directed toward a method and apparatus for sterilizing female mammals. In particular, this invention is directed to a relatively simple surgical procedure for human females which may be performed in the physician's office. Successful implementation of the method results in permanent but not irreversible sterility.

One recognized related surgical technique has been to surgically tie off or sever the fallopian tubes so that the ovum may not pass therethrough, and is thus unavailable for fertilization. A disadvantage of this method is that is is a surgical procedure which requires an incision or which may involve the expense and inconvenience of a hospital stay. Even though office or day surgery may be available in some cases, there is always some risk of complications attendant to this surgery. Further, the method is sometimes not reliable because it is known that the mucosal lining of the fallopian tube characteristically tends to regenerate and resume its function.

Another method involves injecting a curable elastomeric composition into the ovaduct in an amount sufficient to fill the portion of the ovaduct adjacent the uterus. The elastomeric composition is allowed to solidify to thereby nonsurgically block the tube. See for example, Erb, U.S. Pat. No. 3,805,767. Another method of blocking the fallopian tube involved the use of a spherical plug as shown in Read, U.S. Pat. No. 3,042,030. These methods present serious reliability questions.

Yet another method of sterilization involves use of one or more catheter carried hypodermic needles which can be inserted into the uterus to a predetermined position at the uterine cornu and the internal tubal ostra followed by injecting a scarifying or sclerosing agent which produces a chronic lesion at that point. See for example, DeFoe, U.S. Pat. No. 4,416,660. Chemical scarifying of the fallopian tube has also been suggested whereby means is provided for injecting into the fallopian tubes a tissue fibrosing promoting material in combination with the gel-forming carrier. The method promotes tissue fibrosis or scarifying and a permanent closure of the tube. See Corey, U.S. Pat. No. 4,185,618. Peritoneal infiltration by the scarifying agent may occur when using this method.

It is also known that thermoelectric devices are available for performing surgical procedures including, for example, electrically cooled cryocautery devices known as peltier cells. See Hirshhorn, U.S. Pat. No. 3,502,080. However, the device shown in Hirschhorn is not adapted for vaginal cauterization.

SUMMARY OF THE INVENTION

There has been provided a method and apparatus for sterilizing females. Cautery means, vaginally insertable into the fallopian tube of the female, destroys a portion of said mucosal lining at a selected location and exposes an underlying muscle layer. An absorbable scarification means and plug means is placed in the fallopian tube at said selected location. As the scarification means is absorbed, the exposed muscle layer of the fallopian tube forms scar tissue radially thereof whereby the fallopian tube is blocked. The plug means blocks peritoneal infiltration of the by-products of cauterization and scarification outside the fallopian tube during the absorption interval.

DESCRIPTION OF THE PREFERRED EMBODIMENT

Figure 1:
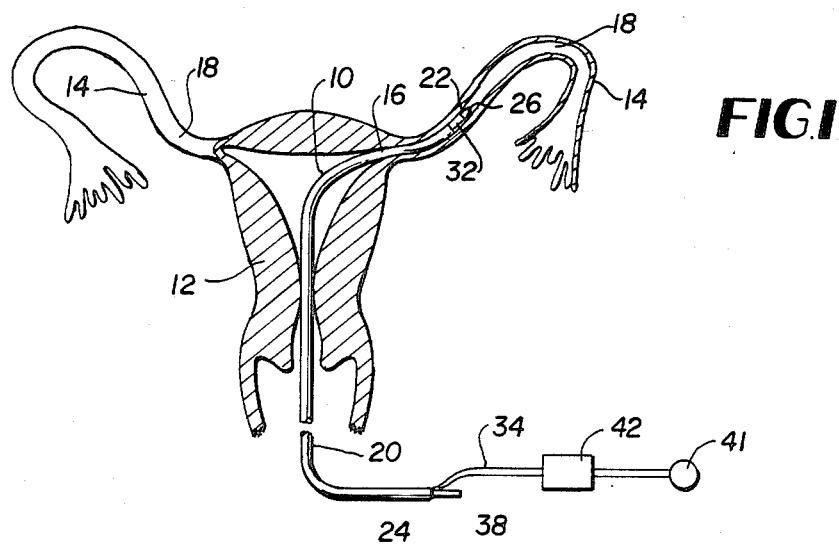
FIG. 1 is a schematic representation of a portion of a human female reproductive system including the uterus and fallopian tubes, showing the device of the present invention inserted in an operative position.
Figure 2:
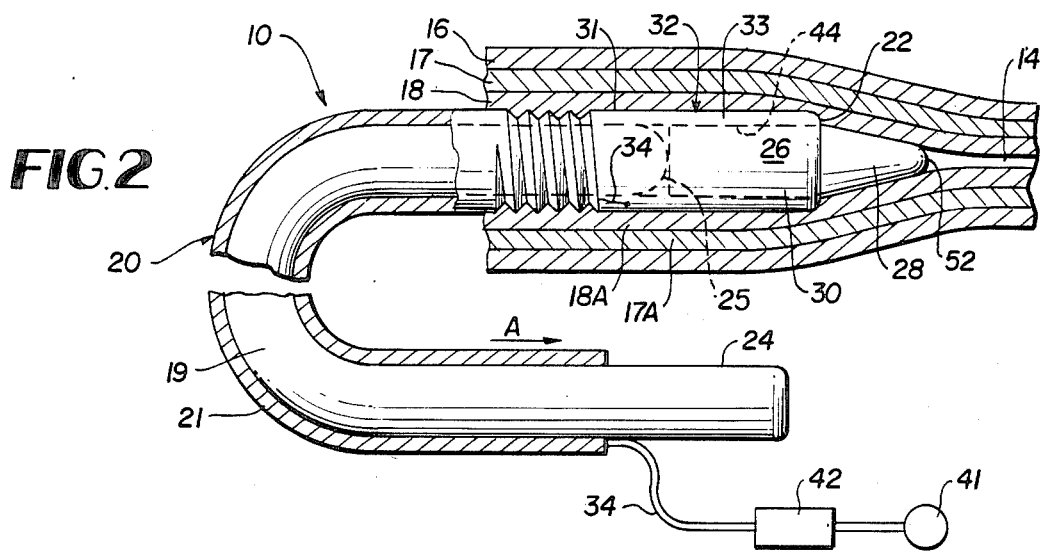
FIG. 2 is a fragmented enlargement of the free or working end of the present invention showing the element in closer detail.

Referring to FIGS. 1 and 2, there is shown schematically a sterilization device 10 of the present invention. In FIG. 1, uterus 12 includes fallopian tubes 14 having an entry or cornul portion 16 between each fallopian tube 14 and the uterus 12. The device 10 is shown vaginally inserted into and extending through the uterus 12 into one fallopian tube 14. The fallopian tubes 14 each have a mucosal lining 18, a muscle layer 17 and a serosa 16 (see FIG. 2). The mucosal lining 18 is particularly resistant to permanent, surgically or thermally induced obstruction and has the characteristic that is particularly resists scarification which tends to block the fallopian tube 14. However, under proper conditions, the muscle layer 17 will scarify so that the fallopian tube 14 will become blocked.

The device 10 of the present invention includes a catheter 20 which has a free or working end 22 and a control end 24. The catheter 20 includes an outer cover member or sleeve 21 and a concentric inner core 19.

The free end 22 of the catheter 20 has a cautery 32 mounted thereto. Preferably the cautery 32 is thermoelectric. More particularly a solid state, electrically energizable cryocautery device known as a peltier cell or peltier device is preferred, and the term will be used hereinafter interchangably with cautery.

A typical peltier cell is comprised of a bimetallic structure. For example, in FIG. 2, the peltier device 32 is formed of a hollow cylindrical copper substrate 33 having a cylindrical recess 44 therein. One surface, for example surface 31 of the substrate 33, may be coated with a different metal such as silver. A cylindrically formed absorbable means 26, hereinafter described, is removeably secured or sleeved within the cylindrical recess 44 of the peltier device 32. Insulated electrical leads 34 are electrically coupled one each to the substrate 33 and the silver surface 31 and extend from the opposite sides of the peltier device 32 internally along the catheter 20 to a suitable source of electrical energy 41 (preferably a D.C. current source not shown) via control 42 (e.g. a current regulator and switch not shown).

Electrical current passed through the two dissimilar metals of substrate 33 and silver surface 31 will cause a thermal effect in the form of heat loss or heat gain based on the amount of and direction of current flow, (i.e. the peltier effect). It is preferred that the peltier device 32 produce a cold effect in a range of temperatures near $-40°$ centigrade sufficient to severely injure or destroy by cauterization a portion of 18A of the mucosal lining 18 in contace with the surface area of the peltier device 32.

The absorbable means 26 is preferably a composite formed of a dilating distal plug portion or plug 28 and an axially adjacent proximal scarification means 30. Because of its particular physical and chemical makeup, the scarification means 30 is sometimes hereinafter referred to as chemoscarification matrix 30. Both the plug 28 and the chemoscarification matrix 30 are preferably formed of absorbable suture material such as polglycolic acid. The chemoscarification matrix 30 also includes an efficacious amount of crystaline copper sulfate in a surface or through matrix with the absorbable material. Over time both polglycolic acid and copper sulfate material are absorbed as hereinafter described.

In operation and as the first step, the catheter 20, carrying the cautery with the absorbable means 26 disposed therein, is inserted vaginally into the patient through the uterus and into position within fallopian tube 14 as shown in FIGS. 1–2. The distal or front end 52 of the plug 28 acts as a dilating probe. When the peltier device 32 is in position, the control 42 is actuated to energize the peltier device 32 whereby a portion 18A of the mucosal lining 18 of the fallopian tube 14 immediately adjacent the peltier device is thermally destroyed or cauterized by a cryogenic thermal exchange. Underlying muscle tissue 17A immediately adjacent the cauterized tissue 18A is thus expose for further treatment in accordance with the present invention. This is one step of the process of the present invention.

Figure 3A:
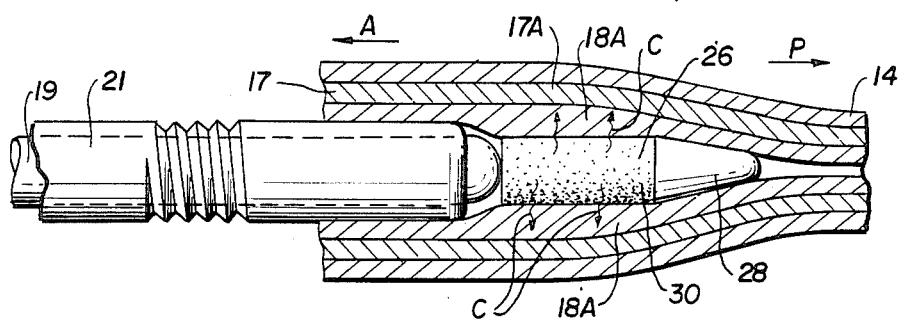
FIG. 3A is a fragmented enlargement of the absorbable means located at the site of thermally destroyed mucosal tissue with the catheter removed.

The next step involved the placement or implantation of the absorbable means at the site of the cauterization. In FIG. 2, the peltier device 32 and the absorbable means 26 coaxial therewith is shown located axially adjacent the destroyed mucosal tissue 18A. The catheter core 19, sleevably located in the cover member or sleeve 21, extends from the control end 24 to a sleeved end 25 in the the peltier device 32. The sleeved end 25 is preferably in abutment with the absorbable means 26 as shown. Relative movement of the core 19 by manually withdrawing the cover 21 causes the peltier device 32 to sleeveably move rearwardly of the sleeved end 25 in the vaginal direction (see Arrow A), such that, the absorbable means 26 in abutment with the sleeved end 25 is sleeveably dislodged from the recess 44 in the peltier device 32 without moving axially. The foregoing is illustrated in FIG. 3A. Although not separately shown, immediately after the placement of the absorbable means 26, the catheter 20 is vaginally withdrawn and the absorbable means 26 remains in place adjacent the destroyed tissue 18A.

Figure 3B:
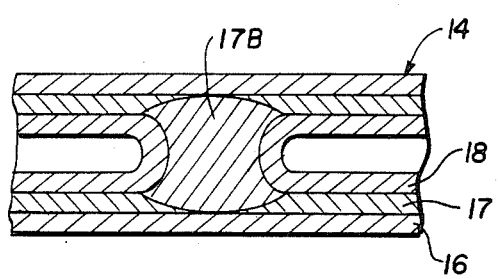
FIG. 3B is a view of the result of scarification and healing of the site in FIG. 3A after the interval of absorption.

The placement of the absorbable means at the site of the destroyed mucosal tissue 18A, as described, exposes underlying muscle tissue 17A of muscle layer 17 to the destructive influence of the copper sulfate crystals. The exposed muscle tissue 17A responds to copper with an intense inflammation and scarring. The response lasts as long as the irritant is present. In the present invention, the copper sulfate crystals are gradually released from the chemoscarification matrix 30 as the matrix is absorbed. The scar results from the tissue filroblasts which are a framework and support for a replacement tissue. The final result, shown in FIG. 3B after absorption of the entire absorbable means 26, is the replacement of muscle fibers in the exposed muscle tissue 17A with a support type or scar tissue 17B that only bridges and does not function as the original tissue. Thus, the destroyed portion of the mucosal lining 18A is replaced by scar tissue 17B proceeding from the exposed muscle tissue 17A thereby resulting in blockage. Accordingly, where there was a hollow tube there is now a solid column. When both fallopian tubes 14 are so treated, the physiologic effect is sterilization.

During the time that the scarification takes place, the serosa 16 remains intact and radially confines the absorbable means 26. Eventually, the chemoscarification matrix 30 is completely absorbed.

As noted above, the leading portion 52 of the plug 28 is shaped so that it functions as a dilator in initial placement. Also, the plug 28 does not contain any copper sulfate crystals. This is an important protective aspect of the invention. As shown in FIG. 3A, the plug 28 does not permit the copper sulfate or other by-products of cauterization (e.g. dead cauterized tissue cells and blood, etc., not shown) to move in the direction of Arrow P and thereby weep into or infiltrate the peritoneal cavity (not shown), and cause unwanted injury or inflamation to bowel or pelvic visera as a consequence of the initial treatment. By this means, the portion of the fallopian tube 14 open to the peritoneal cavity is temporarily sealed while the scarification process proceeds and until the copper sulfate is absorbed by the body.

Permanent injury to the mucosal lining 18 of the fallopian tube 14 is normally difficult to achieve. The lining 18 will heal leaving the fallopian tube 14 virtually intact and operative. The present invention is first designed to cause a portion 18A of the mucosal lining 18 of the fallopian tube 14 to be destroyed to thereby expose a portion of the underlying muscle tissue 17A. With the assistance of the chemoscarification matrix 30 the exposed muscle tissue 17A radially scars causing a permanent blockage thereof. The important feature of the present invention is the destruction of the mucosal lining 18A of the fallopian tube 14 thereby allowing the radially opposing muscle surfaces 17A to be exposed and heal in the presence of an irritating substance so that these surfaces scar thereby producing occlusion of the tube. When the process is complete, the matrix is absorbed, the copper sulfate is absorbed and the tube is scarred closed. Nothing initially placed in the area remains.

The amount of tissue or the length of tube destroyed is controlled. If fertility is again desired, the blocked portion of the fallopian tube 14 shown in FIG. 3B may be surgically removed and a re-anastamosis performed.

The cold or freezing (heat loss) effect of the peltier device 32 has been selected because of its safety and controllability. The copper sulfate also has safety and controllability. The degree of cold, the metals in the peltier device, the composition of the absorbable means, including the scarifying chemicals, and the shape of the plug, are subject to change as circumstances dictate. It should be understood that the foregoing described embodiment is exemplary and prefered, and the invention should not be limited thereby. The method is relatively simple to perform, and does not involve a surgical incision. The method is also inexpensive and reliable and avoids the shortcomings and failures of the described prior arrangements.

What is claimed is:

1. A sterilization device for destroying the mucosal lining of the fallopian tube in females comprising:
   cautery means vaginally insertable into the fallopian tube of the female for destroying a portion of said mucosal lining at a selected location;
   means absorbable over a selected time interval carried with and vaginally insertable simultaneously with said cautery means into the fallopian tube at said selected location including a distal plug means and proximal scarification means, said scarification means for scarifying the fallopian tube radially from a muscular layer thereof, whereby the scarification blocks the fallopian tube and said plug means for blocking peritoneal infiltration of by-products of said cauterization and scarification outside the fallopian tube during the absorption interval.

2. A sterilization device as set forth in claim 1 wherein said cautery means comprises:
   electrically energizable means for providing, when energized, destructive thermal exchange with said mucosal lining for thermally destroying a portion thereof.

3. A device as set forth in claim 1 further comprising:
   a catheter carrying the cautery at a free end for vaginal insertion into the fallopian tube of the female, said catheter having a remotely located control end.

4. A sterilization device as set forth in claim 3 wherein said cautery means has an opening for securing the absorbable means in a distal free end thereof, and the catheter includes means in communication with the opening for dislodging said absorbable means remotely from the distal end of said cautery whereby the catheter and cautery may be removed from the fallopian tube and the absorbable means remains in the vicinity of the thermally destroyed mucosal lining.

5. A sterilization device as set forth in claim 4 wherein said cathether means includes a sleeve and a core slideably mounted therein, one end of the core being in abutment with the absorbable means and a remote end being located near the control end, said sleeve and core being relatively moveable so as to dislodge absorbable means from the cautery adjacent the thermally destroyed mucosal lining.

6. A sterilization device as set forth in claim 1 wherein the scarification means includes copper sulfate.

7. A sterilization device as set forth in claim 1 wherein the absorbable means includes polyglycolic acid.

8. A sterilization device as set forth in claim 1 wherein the absorbable means includes polyglycolic acid and the scarification means further includes copper sulfate in matrix with a portion of said polyglycolic acid.

9. A sterilization device as set forth in claim 1 wherein the cautery means comprises a peltier device.

10. A sterilization device as set forth in claim 9 wherein said peltier device includes a cylindrical metal substrate and having a cylindrical axial forward opening for receiving the absorbable means, said substrate being operatively attached to the catheter means whereby the absorbable means may be dislodged therefrom.

11. A sterilization device as set forth in claim 10 wherein at least one surface of peltier device has a coating of a metal different from the substrate and further comprising: electrical leads, coupled one each to the substrate and the coating, extending externally of the fallopian tube and electrical control means coupled to the leads for electrically energizing the peliter device.

12. A sterilization device set forth in claim 1 wherein said plug means includes a dilating forward end.

13. A vaginally inserted sterilization device for destroying the mucosal lining of the fallopian tube and exposing an underlying portion of a muscle layer thereof in females comprising;
   catheter means having a free end and a remotely located control end;
   cautery means carried by the free end of the catheter means for providing destructive thermal exchange with a portion of said mucosal lining whereby said underlying portion of the muscle layer is exposed; and
   means absorbable over a selected time interval mounted within and forward of said cautery means including chemoscarification means, said chemoscarification means for chemically irritating the exposed muscle layer of the fallopian tube such that scar tissue forms in said tube to thereby block the same, said absorbable means further including plug means at least forward of said chemoscarification means for blocking peritoneal infiltration of by-products of said destructive thermal exchange and scarification.

14. A sterilization device for destroying the mucosal lining of the fallopian tube in females comprising:
   catheter means having a free end which may be vaginally inserted into the fallopian tube of the female and a remotely located control end;
   an electrically energizable cautery means carried by the free end of the catheter means for providing, when energized, destructive thermal exchange with said mucosal lining for thermally destroying a portion thereof;
   absorbable means, absorbable over a selected time interval mounted in a free end of said cautery means, said absorbable means including a distal plug means and proximal chemoscarification means, said chemoscarification means for chemically irritating the fallopian tube radially from a muscular layer thereof, and said plug means for blocking peritoneal infiltration of the scarifying chemical outside the fallopian tube during the absorption interval, whereby the scarification results in blockage of the fallopian tube.

15. A sterilization device as set forth in claim 14 wherein said catheter means includes means in operative relation with the cautery means for dislodging said absorbable means remotely from a free end of said cautery means whereby the catheter may be removed and the absorbable means remains in the vicinity of the thermally destroyed mucosal lining.

16. A sterilization device as set forth in claim 15 wherein said catheter means includes a sleeve and a core slideably mounted therein, one end of the core being in abutment with the absorbable means and a remote end being located near the control end, said sleeve and core being relatively moveable so as to dislodge absorbable means from the cautery means adjacent the thermally destroyed mucosal lining.

17. A sterilization device as set forth in claim 14 wherein the chemoscarification means includes copper sulfate.

18. A sterilization device as set forth in claim 14 wherein the absorbable means includes polyglycolic acid.

19. A sterilization device as set forth in claim 14 wherein the absorbable means includes polyglycolic acid and the chemoscarification means further includes copper sulfate in matrix with a portion of said polyglycolic acid.

20. A sterilization device as set forth in claim 14 wherein the cautery means comprises a peltier device.

21. A sterilization device as set forth in claim 20 wherein said peltier device includes a cylindrical metal substrate and having a cylindrical axial forward opening for receiving the absorbable means, said substrate being operatively attached to the catheter means whereby the absorbable means may be dislodged therefrom.

22. A sterilization device as set forth in claim 21 wherein at least one surface of peltier device has a coating of a metal different from the substrate and further comprising: electrical leads, coupled on each to the substrate and the coating, extending to the control end and electrical control means coupled to the leads for electrically energizing the peltier device.

23. A sterilization device set forth in claim 14 wherein said plug includes a dilating forward end.

24. A sterilization device as set forth in claim 14 wherein the plug means has a rounded dilating forward free end, said plug means for dilating passages through which the catheter means is passed and for blocking peritoneal infiltration of the scarifying material outside the fallopian tube during absorption of the chemoscarification means.

25. A method of sterilizing human females by destroying the mucosal lining of the fallopian tube comprising the steps of: vaginally inserting a cautery device together simultaneously with an absorbable means into the fallopian tube at a selected location; cauterizing a portion of the fallopian tube by said cautery device to destroy a portion of said mucosal lining and exposing an underlying portion of muscle tissue; exposing within said fallopian tube at the location of the cauterized portion thereof said absorbable means including a distal plug and chemoscarifying means upstream of said plug for scarifying and exposed muscle tissue of the fallopian tube radially thereof; and blocking peritoneal infiltration of by-products associated with said cauterization and scarification by means of said distal plug.

26. A method of sterilizing human females by destroying the mucosal lining of the fallopian tube comprising the steps of: vaginally inserting an electrically energizable cryocautery device together simultaneously with an absorbable means into the fallopian tube; thermally destroying a portion of the tube by activating said cryocautery device; exposing to said thermally destroyed tube portion within said fallopian tube said absorbable means including a plug downstream of said thermally destroyed tissue and chemoscarifying means upstream of said plug adjacent the thermally destoryed tissue for chemically irritating the fallopian tube radially from a muscular layer thereof in situ adjacent the thermally destroyed tube; retaining within the fallopian tube by means of said plug, chemicals associated with said scarification means so that scarification proceeds from a muscular layer of the fallopian tube whereby a blockage occurs in said fallopian tube for sterilizing the female.

* * * * *